US012150750B2

(12) United States Patent
Xu et al.

(10) Patent No.: US 12,150,750 B2
(45) Date of Patent: Nov. 26, 2024

(54) D-GLUCOSE AND ITS ANALOGS AS TRACERS TO ASSESS THE GLUCOSE TRANSPORTER FUNCTION ON BLOOD-CEREBROSPINAL FLUID BARRIER AND THE FUNCTIONING OF THE BRAIN LYMPHATIC SYSTEM

(71) Applicant: The Johns Hopkins University, Baltimore, MD (US)

(72) Inventors: Jiadi Xu, Timonium, MD (US); Peter Van Zijl, Hanover, MD (US); Lin Chen, Baltimore, MD (US); Kannie Wai Yan Chan, Hong Kong (CN); Jianpan Huang, Hong Kong (CN)

(73) Assignees: The Johns Hopkins University, Baltimore, MD (US); Kennedy Krieger Institute, Baltimore, MD (US); City Iniversity of Hong Kong, Kowloon (HK)

( * ) Notice: Subject to any disclaimer, the term of this patent is extended or adjusted under 35 U.S.C. 154(b) by 115 days.

(21) Appl. No.: 17/918,031

(22) PCT Filed: Apr. 7, 2021

(86) PCT No.: PCT/US2021/026217
§ 371 (c)(1),
(2) Date: Oct. 10, 2022

(87) PCT Pub. No.: WO2021/207382
PCT Pub. Date: Oct. 14, 2021

(65) Prior Publication Data
US 2023/0126413 A1    Apr. 27, 2023

Related U.S. Application Data

(60) Provisional application No. 63/006,952, filed on Apr. 8, 2020.

(51) Int. Cl.
*A61B 5/055*     (2006.01)
*G01R 33/565*   (2006.01)
*G01R 33/483*   (2006.01)

(52) U.S. Cl.
CPC ........... *A61B 5/055* (2013.01); *G01R 33/565* (2013.01); *G01R 33/4833* (2013.01)

(58) Field of Classification Search
CPC ...... A61B 5/055; A61B 5/414; G01R 33/565; G01R 33/4833
See application file for complete search history.

(56) References Cited

U.S. PATENT DOCUMENTS

2016/0287714 A1 * 10/2016 Kataoka ................... B01J 13/02
2017/0216413 A1 *  8/2017 Quinn .................. C12N 9/2402

FOREIGN PATENT DOCUMENTS

RU    2697994 C2    8/2019
RU    2703393 C1   10/2019
(Continued)

OTHER PUBLICATIONS

Xu et al., GlucoCEST Imaging with On-Resonance Variable Delay Multiple Pulse (onVDMP) MRI, Magn Reson Med. Jan. 2019 ; 81(1): 47-56. doi:10.1002/mrm.27364.*
(Continued)

*Primary Examiner* — Bo Joseph Peng
(74) *Attorney, Agent, or Firm* — Venable LLP; Henry J. Daley (57) ABSTRACT

A method of assessing the brain lymphatic or glymphatic system and the glucose transporter function on blood-cerebrospinal fluid barrier (BCSFB) of a subject using D-glucose or a D-glucose analog. A spatial map is generated of water MR signals that are sensitized to changes in D-glucose or a D-glucose analog in cerebrospinal fluid (CSF) of the subject. The spatial map is observed at one or more time points
(Continued)

before, one or more time points during, and one or more time points after, raising the blood level of the D-glucose or a D-glucose analog in the subject CSF. A difference is detected between the MR signals of the spatial map before, during, and after raising the blood level of D-glucose or a D-glucose analog. A physiological parameter associated with the brain lymphatic or glyphatic system and the glucose transporter function on BCSFB of the subject is ascertained based on the detected difference.

16 Claims, 5 Drawing Sheets

(56) References Cited

FOREIGN PATENT DOCUMENTS

| | | |
|---|---|---|
| WO | 2016/104664 A1 | 6/2016 |
| WO | 2016/173861 A1 | 11/2016 |

OTHER PUBLICATIONS

Xu et al., On-resonance Variable Delay Multi Pulse Scheme for Imaging of Fast-exchanging Protons and semi-solid Macromolecules, Magn Reson Med. Feb. 2017 ; 77(2): 730-739. doi:10.1002/mrm.26165.*

Tolomeo et al., Chemical exchange saturation transfer MRI shows low cerebral 2-deoxy-D-glucose uptake in a model of Alzheimer's Disease, Sci Rep. Jun. 22, 2018;8(1):9576. doi: 10.1038/s41598-018-27839-7. PMID: 29934551; PMCID: PMC6015016.*

Daoust et al., Transverse relaxation of cerebrospinal fluid depends on glucose concentration, Magnetic Resonance Imaging 44 (2017) 72-81, https://doi.org/10.1016/j.mri.2017.08.001.*

Iliff et al., "A paravascular Pathway Faciliates CSF Flow Through the Brain Parenchyma and the Clearance of Interstitial Solutes, Including Amyloid beta", Sci Transl Medicine., (Aug. 15, 2012), vol. 4, Issue 147, (12 pages).

Xu et al., "Deletion of aquaporin-4 in APP/PS1 mice exacerbates brain Abeta accumulation and memory deficits", Mol Neurodegeneration., (2015), vol. 10, (16 pages).

Xie et al., "Sleep Drives Metabolite Clearance from the Adult Brain", Science., (Oct. 18, 2013), vol. 342, pp. 373-377.

Ramussen et al., "The glymphatic pathway in neurological disorders", Lancet Neurology., (Nov. 2018), vol. 17, pp. 1016-1024.

Louveau et al., "Lymphatics in Neurological Disorders: A Neuro-Lympho-Vascular Component of Multiple Sclerosis and Alzheimer's Disease?", Neuron., (Sep. 7, 2016), vol. 91, pp. 957-973.

Da Mesquita et al., Functional aspects of meningeal lymphatics in ageing and Alzheimer's disease, Nature., (Aug. 9, 2018), vol. 560, pp. 185-191.

Absinta et al., "Human and nonhuman primate meninges harbor lymphatic vessels that can be visualized noninvasively by MRI", Elife., (2017), vol. 6, (15 pages).

Harrison et al., "Non-invasive imaging of CSF-mediated brain clearance pathways via assessment of perivascular fluid movement with diffusion tensor MRI", Elife., (2018), vol. 7, (14 pages).

Taoka et al., "Evaluation of glymphatic system activity with the diffusion MR technique: diffusion tensor image analysis along the perivascular space (DTI-ALPS) in Alzheimer's disease cases", Jpn J Radiology., (2017), pp. 172-178, vol. 35, pp. 172-178.

Ohene et al., "Non-invasive MRI of brain clearance pathways using multiple echo time arterial spin labelling: an aquaporin-4 study", Neuroimage., (2019), vol. 188, pp. 515-523.

Kuo et al., "Meningeal Lymphatic Vessel Flow Runs Countercurrent to Venous Flow in the Superior Sagittal Sinus of the Human Brain", Tomography., (2018), vol. 4, No. 3, pp. 99-104.

Iliff et al., "Brain-wide pathway for waste clearance captured by contrast-enhanced MRI", J Clinical Invest., (Mar. 2013), vol. 123, No. 3, pp. 1299-1309.

Gaberel et al., "Impaired Glyphatic Perfusion After Strokes Revealed by Contrast-Enhanced MRI: A New Target for Fibrinolysis", Stroke., (2014), vol. 45, pp. 3092-3096.

Lee et al., "Quantitative Gd-DOTA Uptake From Cerebrospinal Fluid into Rat Brain Using 3D VFA-SPGR at 9.4T", Magn Reson Med., (2018), vol. 79, pp. 1568-1578.

Ringstad et al., "Brain-wide glymphatic enhancement and clearance in humans assessed with MRI", JCI Insight., (2018), vol. 3, No. 13, (17 pages).

Eide et al., "MRI with intrathecal MRI gadolinium contrast medium administration: a possible method to assess glymphatic function in human brain", Acta Radiol Open., (2015), vol. 4, No. 11, (5 pages).

Ringstad et al., "Glymphatic MRI in idiopathic normal pressure hydrocephalus", Brain., (2017), vol. 140, pp. 2691-2705.

Taoka et al., "Gadolinium-based Contrast Media, Cerebrospinal Fluid and the Glymphatic System: Possible Mechanisms for the Deposition of Gadolinium in the Brain", Magn Reson Med Sci., (Jan. 25, 2018), vol. 17, pp. 111-119.

McDonald et al., "Intracranial Gadolinium Deposition after Contrast-enhanced MR Imaging", Radiology., (Jun. 2015), vol. 275, No. 3, pp. 772-782.

Simpson et al., "Decreased Concentrations of GLUT1 and GLUT3 Glucose Transporters in the Brains of Patients with Alzheimer's Disease", Ann Neurology., (1994), pp. vol. 35, 546-551.

Mooradian et al., "GLUT-1 Expression in the Cerebra of Patients with Alzheimer's Disease", Neurobiol Aging., (1997), vol. 18, No. 5, pp. 469-474.

Nordberg et al., "The use of PET in Alzheimer's disease", Nature Reviews Neurology., (Feb. 2010), vol. 6, (10 pages).

Kato et al., "Brain fluorodeoxyglucose (FDG) PET in dementia", Ageing research reviews., (2016), vol. 30, pp. 73-84.

Schwartz et al., "Metabolic Mapping of Functional Activity in the Hypothalamusophysial System of the Rat", Science., (Aug. 17, 1979), vol. 205, pp. 723-725.

Phelps et al., "Study of Cerebral Function with Positron Computed Tomography", J Cereb Blood Flow Metab., (1982), vol. 2, pp. 113-162.

Van Zijl et al., "In Vivo Proton Spectroscopy and Spectroscopic Imaging of {1-13C}-Glucose and its Metabolic Products", Magn Reson Med., (1993), vol. 30, pp. 544-551.

Van Zijl et al., "Determination of cerebral glucose transport and metabolic kinetics by dynamic MR spectroscopy", Am J Physiology., (1997), pp. E1216-E1227.

Xin et al., "Assessment of metabolic fluxes in the mouse brain in vivo using 1H-13C NMR spectroscopy at 14.1 Tesla", J Cereb Blood Flow Metab., (2015), vol. 35, (7 pages).

Mason et al., "NMR Determination of the TCA Cycle Rate and alpha-Ketoglutarate/Glutamate Exchange Rate in Rat Brain", J Cereb Blood Flow Metab., (1992), vol. 12, pp. 434-447.

Gruetter et al., "Broadband Decoupled, 1H-Localized 13C MRS of the Human Brain at 4 Tesla", Magn Reson Med., (1996), vol. 36, pp. 659-664.

De Graaf et al., "In vivo 1H-13C-NMR spectroscopy of cerebral metabolism", NMR Biomed., (2003), vol. 16, pp. 339-357.

Henry et al., "In vivo 13C NMR spectroscopy and metabolic modeling in the brain: a practical perspectiv"., Magn Reson Imaging., (2006), vol. 24, pp. 527-539.

Nabuurs et al., "Localized Sensitivity Enhanced In Vivo 13C MRS to Detect Glucose Metabolism in the Mouse Brain", Magn Reson Med., (2008), vol. 59, pp. 626-630.

Du et al., "Simultaneous measurement of glucose blood-brain transport constants and metabolic rate in rat brain using in vivo H-1 MRS", J Cerebr Blood F Met., (2012), vol. 32, pp. 1778-1787.

Gruetter et al., "1H NMR Studies of Glucose Transport in the Human Brain", J Cereb Blood Flow Metab., (1996), vol. 16, pp. 427-438.

De Feyter et al., "Deuterium metabolic imaging (DMI) for MRI-based 3D mapping of metabolism in vivo", Science Advances., (Aug. 22, 2018), vol. 4, (12 pages).

Chan et al., "Natural D-Glucose as a Biodegradable MRI Constant Agent for Detecting Cancer", Magn Reson Med., (2012), vol. 68, pp. 1764-1773.

(56) References Cited

OTHER PUBLICATIONS

Walker-Samuel et al., "In vivo imaging of glucose uptake and metabolism in tumors", Nature Medicine., (Aug. 2013), vol. 19, No. 8, (8 pages).
Yadav et al., "Natural D-Glucose as a Biodegradable MRI Relaxation Agent", Magn Reson Med., (2014), vol. 72, pp. 823-828.
Jin et al., "Mapping brain glucose uptake with chemical exchange-sensitive spin-lock magnetic resonance imaging", J Cereb Blood Flow Metab., (2014), vol. 34, pp. 1402-1410.
Jin et al., "Chemical exchange-sensitive spin-lock MRI of glucose analog 3-O-methyl-D-glucose in normal and ischemic brain", J Cereb Blood Flow Metab., (2018), vol. 38, pp. 869-880.
Paech et al., "T1rho-weighted Dynamic Glucose-enhanced MR Imaging in the Human Brain", Radiology., (Dec. 2017), vol. 285, No. 3, pp. 914-922.
Xu et al., "On-Resonance Variable Delay Multipulse Scheme for Imaging of Fast-Exchanging Protons and Semisolid Macromolecules", Magn Reson Med., (2017), vol. 77, pp. 730-739.
Xu et al., "On Resonance VDMP Technique for Improved glucoCEST Detection in Brain Tumors", Proc 24th Meeting ISMRM., (2016), (3 pages).
Wu et al., "Dynamic glucose enhanced MRI of the placenta in a mouse model of intrauterine inflammation", Placenta., (2018), vol. 69, pp. 86-91.
Chen et al., "Creatine and phosphocreatine mapping of mouse skeletal muscle by a polynominal and Lorentzian line-shape fitting CEST method", Magn Reson Med., (2019), vol. 81, pp. 69-78.
Chen et al., "Investigation of the contribution of total creatine to the CEST Z-spectrum of brain using a knockout mouse model", NMR Biomed., (2017), vol. 30, (12 pages).
Li et al., "The neuritic plaque faciliates pathological conversion of tau in an Alzheimer's disease mouse model", Nature Communications., (2016), vol. 7, (13 pages).
Trott et al., "1p Relaxation outside of the Fast-Exchange Limit", J Magn Reson., (2002), vol. 154, pp. 157-160.
Trott et al., "Theoretical study of R(1rho) rotating-frame and R2 free-precession relaxation in the presence of n-site chemical exchange", J Magn Reson., (2004), vol. 170, pp. 104-112.
Jin et al., "Spin-Locking Versus Chemical Exchange Saturation Transfer MRI for Investigating Chemical Exchange Process Between Water and Labile Metabolite Protons", Magn Reson Med., (2011), vol. 65, pp. 1448-1460.
Jin et al., "Chemical exchange-sensitive spin-lock (CESL) MRI of glucose and analogs in brain tumors", Magn Reson Med., (2018), vol. 80, pp. 488-495.

Schuenke et al., "Adiabatically Prepared Spin-Lock Approach for T1rho-Based Dynamic Glucose Enhanced MRI at Ultrahigh Fields", Magn Reson Med., (2017), vol. 78, pp. 215-225.
Xu et al., "Dynamic Glucose Enhanced (DGE) MRI for Combined Imaging of Blood-Brain Barrier Break Down and Increased Blood Volume in Brain Cancer", Magn Reson Med., (2015), vol. 74, pp. 1556-1563.
Myronenko et al., "Intensity-Based Image Registration by Minimizing Residual Complexity", IEEE Trans Med Imaging., (Nov. 2010), vol. 29, No. 11, pp. 1882-1891.
Zu et al., "Measurement of regional cerebral glucose uptake by magnetic resonance spin-lock imaging", Magn Reson Imaging., (2014), vol. 32, pp. 1078-1084.
Gore et al., "Influence of Glycogen on Water Proton Relaxation-Times", Magn Reson Med., (1986), vol. 3, pp. 463-466.
Liu et al., "Decreased glucose transporters correlate to abnormal hyperphosphorylation of tau in Alzheimer's disease", FEBS Letters., (2008), vol. 582, pp. 359-364.
Winkler et al., "GLUT1 reductions exacerbate Alzheimer's disease vasculo-neuronal dysfunction and degeneration", Nature Neuroscience., (Apr. 2015), vol. 18, No. 4, pp. 521-530.
Knutsson et al., "Arterial Input Functions and Tissue Response Curves in Dynamic Glucose-Enhanced (DGE) Imaging: Comparison Between glucoCEST and Blood Glucose Sampling in Humans", Tomography., (Dec. 2018), vol. 4, No. 4, pp. 164-171.
Ma et al., "Outflow of cerebrospinal fluid is predominantly through lymphatic vessels and is reduced in aged mice", Nature Communications., (2017), vol. 8, (13 pages).
Ahn et al., "Meningeal lymphatic vessels at the skull base drain cerebrospinal fluid", Nature, (Aug. 1, 2019), vol. 572, pp. 62-66.
Benner et al., "Accuracy of Gamma-Variate Fits to Concentration-Time Curves From Dynamic Susceptibility-Contrast Enhanced MRI: Influence of Time Resolution, Maximal Signal Drop and Signal-to-Noise", Magn Reson Imaging., (1997), vol. 15, No. 3, pp. 307-317.
Orton et al., "Computationally efficient vascular input function models for quantitative kinetic modeling using DCE-MRI", Phys Med Biol., (2008), vol. 53, pp. 1225-1239.
Peng et al., "Suppression of glymphatic fluid transport in a mouse model of Ahzlheimer's disease", Neurobiol Disease., (2016), vol. 93, pp. 215-225.
Liu et al., "A dextran-based probe for the targeted magnetic resonance imaging of tumours expressing prostate-specific membrane antigen", Nature Biomedical Engineering., (Dec. 2017), vol. 1, pp. 977-982.

* cited by examiner

D-GLUCOSE AND ITS ANALOGS AS TRACERS TO ASSESS THE GLUCOSE TRANSPORTER FUNCTION ON BLOOD-CEREBROSPINAL FLUID BARRIER AND THE FUNCTIONING OF THE BRAIN LYMPHATIC SYSTEM

CROSS-REFERENCE OF RELATED APPLICATION

This application is a U.S. National Stage Application of PCT/US2021/026217, filed Apr. 7, 2021, which claims priority to U.S. Provisional Application No. 63/006,952, filed Apr. 8, 2020, the entire contents of which are hereby incorporated by reference.

This invention was made with government support under grant numbers P41EB015909, R01EB019934 and R01EB015032 awarded by the National Institute of Health/National Center for Biotechnology Information. The government has certain rights in the invention.

BACKGROUND

1. Technical Field

Some embodiments relate to systems and methods for assessing the glucose transporter function on the blood-cerebrospinal barrier and the function of the brain lymphatic system.

2. Discussion of Related Art

The brain lymphatic system, known as the glymphatic system, is a recently discovered cerebrospinal fluid (CSF) circulation system that utilizes the perivascular channels to eliminate the soluble protein and metabolite wastes and to distribute other compounds, such as glucose, lipids, and amino acids, in the brain (1). The subarachnoid CSF that is secreted by the choroid plexus of the cerebral ventricles will recirculate through the brain parenchyma through this glymphatic system and exchange with the interstitial fluid (ISF). More and more evidence suggests that this pathway appears important for the clearance of soluble amyloid beta (Aβ) from the brain parenchyma (2-5). The dysfunction of the glymphatic system not only promotes AP deposition in the meninges but also introduces perfusion reduction and cognitive impairment as evidenced on animal studies (6). Hence, it is important to develop a clinically applicable prognostic tool for measuring glymphatic function that is usable for the diagnosis and evaluation of Alzheimer's Disease (AD) and possibly other neurodegenerative diseases, such as Huntington's Disease (HD) and Parkinson's Disease (PD) among others.

The glymphatic examination includes the direct visualization of glymphatic vessels and the CSF-ISF exchanging process through the glymphatic pathways. The existence of meningeal lymphatic vessels in human and nonhuman has been confirmed by magnetic resonance imaging (MRI) with gadolinium-based contrast agents (7). Imaging of the glymphatic system is an emerging field, and many non-invasive MRI techniques have been developed such as diffusion based methods (8,9), a T2 based ASL method (10) and a time-of-flight based MRI method (11). The above non-invasive MRI methods are still limited to the determination of CSF flow in the glymphatic vessels or in the ventricles since the CSF-ISF exchange process is extremely slow. Examination of the CSF-ISF exchange process by MRI is mainly achieved by intra-cranial (6, 12-14) or intrathecal injection (15-17) of gadolinium-based contrast agents. Although, the intrathecal injection has been applied on human studies, it is still a highly invasive method and might not be ideal for routine and repeated measurements on patients. Also the safety of Gadolinium based agents is still a concern as they may be retained in the deep gray matter nuclei for longer periods of time (18,19). Therefore, there remains a need for systems and methods for assessing the function of the blood-cerebrospinal fluid barrier and the function of the brain lymphatic system.

SUMMARY

Some embodiments provide a method of assessing the brain lymphatic or glymphatic system and the glucose transporter function on blood-cerebrospinal fluid barrier (BCSFB) of a subject using D-glucose or a D-glucose analog. The method includes generating a spatial map of water magnetic resonance (MR) signals that are sensitized to changes in D-glucose or a D-glucose analog in cerebrospinal fluid (CSF) of the subject; observing the spatial map at one or more time points before, one or more time points during, and one or more time points after, raising the blood level of the D-glucose or a D-glucose analog in the subject CSF; detecting a difference between the MR signals of the spatial map before, during, and after raising the blood level of D-glucose or a D-glucose analog; and ascertaining a physiological parameter associated with the brain lymphatic or glymphatic system and the glucose transporter function on BCSFB of the subject based on the detected difference.

According to some embodiments, the D-glucose analog is a sugar that is transported from the blood into the CSF. According to some embodiments the D-glucose analog is at least one of 2-deoxy-D-glucose (2DG), glucosamine, 3-O-methyl-Dglucose (3OMG), Vitamin C, fluorodeoxyglucose (FDG), or mannitol. According to some embodiments, the sensitizing to changes in D-glucose or a D-glucose analog includes applying one or more radiofrequency (RF) pulses at one or multiple frequencies around the resonance frequency of water.

According to some embodiments, the method further includes determining the rate of change and amplitude of the MR signal due to the presence of the D-glucose or a D-glucose analog. According to some embodiments, the method further includes determining the glucose transporter function on the BCSFB based on the rate of change and amplitude of the MR signal. According to some embodiments, the method further includes determining the clearance or decay rate and amplitude of the MR signal change due to the D-glucose or D-glucose analog. According to some embodiments, the method further includes assessing the brain lymphatic or glymphatic system based on the clearance or decay rate and amplitude of the MR signal change. According to some embodiments, the applying one or more RF pulses is such that the MR signal changes after infusion of D-glucose or D-glucose analog are determined predominantly by a change in relaxation (T2 or T1p) of the water signal due to the chemical exchange of hydroxyl protons in the D-glucose or D-glucose analog with the water protons detected in magnetic resonance imaging (MRI). According to some embodiments, the applying one or more RF pulses is such that MRI signal changes after a D-glucose or a glucose analog infusion are introduced by selective saturation of at least one exchangeable group in the D-glucose or D-glucose analog. According to some embodiments, the RF pulses include a sequence of high-power short radiofrequency pulses separated by inter-pulse delay periods of equal or different length with carrier frequencies set at a water resonance frequency.

According to some embodiments, the inter pulse delay periods range from 0 to several hundred milliseconds. According to some embodiments, the high-power pulses comprise adiabatic or hard excitation pulses. According to some embodiments, the high-power pulses include a train of composite pulses with shifted phases causing an excitation profile that magnetically labels exchanging protons in D-glucose or D-glucose analogs. According to some embodiments, the high-power pulses include spin-lock pulses. According to some embodiments, the RF pulses are applied according to at least one of an on-resonance variable delay multiple pulse (onVDMP) scheme, a spin-lock scheme, or a Carr-Purcell-Meiboom-Gill (CPMG) scheme.

Some embodiments provide a method of applying a pulse sequence of radiofrequency (RF) pulses having different time delays; applying the pulse sequence at multiple selected frequencies; analyzing a difference in signal change as a function of post-sugar infusion time based on the applied pulse sequence; analyzing a difference in phase change as a function of post-sugar infusion time based on the applied pulse sequence; generating images of the differences in signal change as a function of post-sugar infusion time; and generating images of the differences in phase change as a function of post-sugar infusion time.

According to some embodiments, the RF pulses include a sequence of high-power short radiofrequency pulses separated by inter-pulse delay periods of equal or different length with carrier frequencies set at a water resonance frequency. According to some embodiments the RF pulses are applied according to at least one of an on-resonance variable delay multiple pulse (onVDMP) scheme, a spin-lock scheme, or a Carr-Purcell-Meiboom-Gill (CPMG) scheme.

Some embodiments provide a magnetic resonance (MR) system that includes a magnet system configured to provide a substantially homogeneous magnetic field over an imaging volume in a subject's brain. The system also includes a magnetic field gradient system arranged proximate to the imaging volume, where the magnetic field gradient coil is configured to generate spatial encoding in the substantially homogeneous magnetic field. The system also includes a radiofrequency (RF) system arranged proximate to the imaging volume so as to be able to acquire a plurality of water MR signals that are sensitized to changes in at least one of D-glucose and a D-glucose analog in cerebrospinal fluid (CSF) of the subject's brain. A data processor of the system is configured to communicate with the RF system to receive the MR signals. The data processor is further configured to generate, based on the received MR signals, multiple dynamic glucose enhancement measurements corresponding to multiple time intervals, the time intervals including at least two of a time interval prior, during, and after administration of at least one of D-glucose and the D-glucose analog to the subject.

BRIEF DESCRIPTION OF THE DRAWINGS

Further objectives and advantages will become apparent from a consideration of the description, drawings, and examples.

DETAILED DESCRIPTION

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The below-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described. The references cited anywhere in this specification are hereby incorporated by reference as if each had been individually incorporated.

Figure 1:
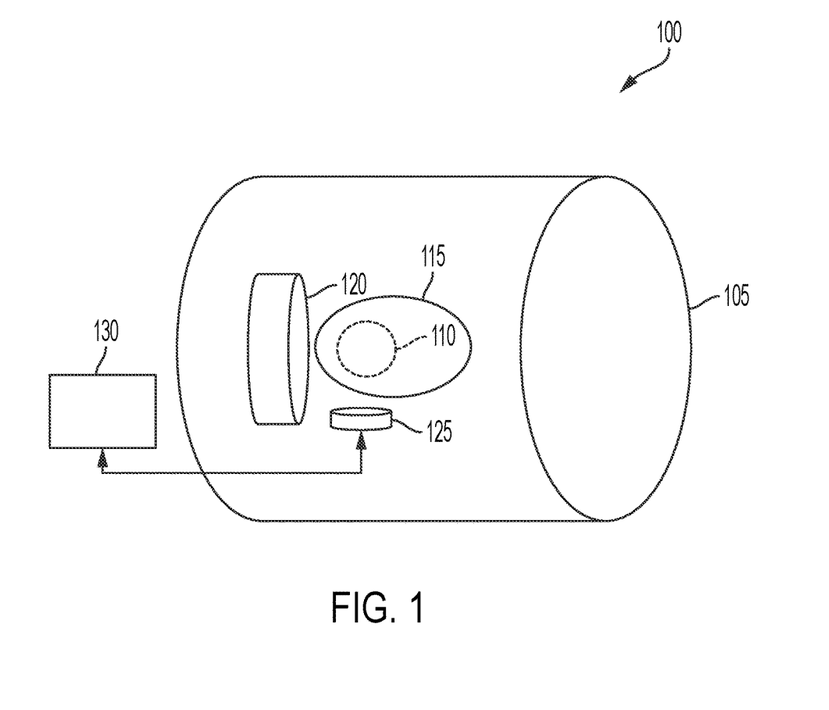
FIG. 1 illustrates a magnetic resonance (MR) system 100 of some embodiments.

FIG. 1 illustrates a magnetic resonance (MR) system 100 of some embodiments that includes a magnet system 105 configured to provide a substantially homogeneous magnetic field over an imaging volume 110 in a subject's brain 115. The system of some embodiments also includes a magnetic field gradient system 120 (e.g., a gradient coil) arranged proximate to the imaging volume 110, where the magnetic field gradient coil is configured to generate spatial encoding in the substantially homogeneous magnetic field. The system of some embodiments also includes a radiofrequency (RF) excitation and detection system 125 arranged proximate to the imaging volume 110 so as to be able to acquire a plurality of water MR signals that are sensitized to changes in at least one of D-glucose and a D-glucose analog in cerebrospinal fluid (CSF) of the subject's brain 115. In some embodiments, a data processor 130 of the system is configured to communicate with the RF excitation and detection system 125 to receive the MR signals. The data processor 130 is further configured to generate, based on the received MR signals, multiple dynamic glucose enhancement measurements corresponding to multiple time intervals, the time intervals including at least one of a time interval prior, during, and after administration of at least one of D-glucose and the D-glucose analog to the subject, as discussed in further detail below.

According to certain embodiments, the glymphatic pathway is assessed using D-glucose, or a D-glucose analog, as a natural biodegradable contrast agent. Glucose transport protein (e.g., GLUT-1, GLUT-3, etc.) that carry glucose molecules through the blood brain barrier is highly enriched in brain capillary endothelial cells. Hence, D-glucose easily penetrates the blood-brain barrier (BBB) and blood-CSF barriers (BCSFB) and goes into CSF. After entering the CSF through the blood-cerebrospinal fluid barrier (BCSFB), glucose is recirculated to the parenchyma through the glymphatic pathway as demonstrated in FIG. 2 (20).

Figure 2:
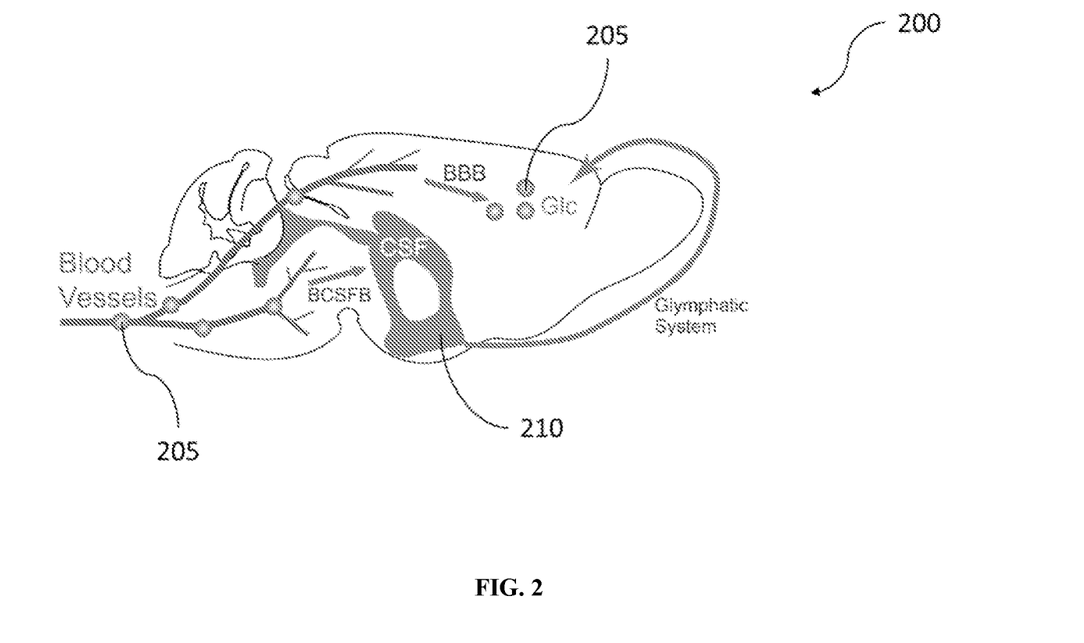
FIG. 2 illustrates the glucose transport pathways in a mouse brain after intravenous infusion of glucose.

FIG. 2 illustrates the glucose transport pathways in a mouse brain 200 after intravenous infusion of glucose. Glucose 205 in blood crosses the blood-brain barrier (BBB)'s luminal and abluminal membranes and reaches parenchyma. Part of the glucose rapidly enters the CSF 210 through the blood-cerebrospinal fluid barrier (BCSFB) and recirculates to the parenchyma through the glymphatic system.

The glucose provides an opportunity in some embodiments to monitor the CSF-ISF exchanging process through the intravenous administration of glucose, a much less invasive method compared to intrathecal injection. Since the uptake rate of glucose in CSF is determined by the glucose transporters, which are known to be affected by the onset of AD symptoms (21,22), the glucose uptake curves in both CSF and brain parenchyma are also used in some embodiments to assess changes in glucose transport protein concentration or functioning on BBB and BCSFB in AD patients, respectively.

The major difficulty in applying glucose as a tracer for assessing glymphatic pathway is the detection of the glucose signal with sufficient sensitivity. Currently, glucose uptake in the brain is assessed non-invasively using 2-[$^{18}$F]fluoro-2-deoxy-D-glucose positron emission tomography (FDG-PET) (23,24). Despite its great detection sensitivity, the high-cost and limited availability of FDG-PET hamper its wide clinical application. In addition, the use of a radioactive tracer is not ideal for repeated measurements, especially when combined with computer tomography (CT) for anatomical referencing (25,26) adding more radiation exposure. Furthermore, the limited resolution of a PET scan will be challenging for detecting glucose in ventricles due to their small size.

An alternative way to measure glucose uptake and utilization is $^{13}$C and $^1$H in vivo magnetic resonance spectroscopy (MRS) (27-36), as well as a recent deuterium metabolic imaging (DMI) method (37). The limited sensitivity of the MRS methods also make the detection of glucose in CSF extremely challenging. Recently, a glucose chemical exchange saturation transfer (glucoCEST) MRI technique was developed to detect the unlabeled glucose at the physiological relevant concentration by monitoring the water signal reduction due to the chemical exchange process after saturating the hydroxyl groups in glucose. (38,39) Alternative methods, such as T2 relaxation (40) and spin-lock (41-43) were also applied for mapping glucose uptake in brain by making use of the chemical exchanging process of the glucose hydroxyl protons.

In some embodiments, a novel on-resonance labeling strategy is used to improve the labeling efficiency (44-46) with much improved sensitivity in detecting glucose comparing to conventional glucoCEST. Another factor that suppresses the CEST signal in tissues is the strong scaling effect due to the abundant macromolecules in tissue as suggested by a recent study on in vivo creatine and phosphocreatine CEST (47,48). When detecting glucose in CSF, this scaling effect will be minimized since only trace amounts of protein are present in CSF. Furthermore, the T1 of CSF (around 3.4 s at 11.7 T) is also much longer than tissues (around 2 s at 11.7 T), which will lead to a higher CEST signal. In some embodiments, all these beneficial factors are combined, with a much higher glucose CEST signal expected to be detected in CSF with the on-resonance variable delay multi pulse (onVDMP) method, spin-lock (41-43) and Carr-Purcell-Meiboom-Gill (CPMG) MRI methods, and standard RF saturation. These techniques require in some embodiments a substantially homogeneous magnetic field (e.g., the main magnetic field B0, or the RF field B1) over the imaging volume, so that image artifacts are prevented/reduced and to achieve accurate magnetic labeling. The homogeneity of these magnetic fields is achieved in some embodiments by field mapping and shimming techniques.

Figure 3:
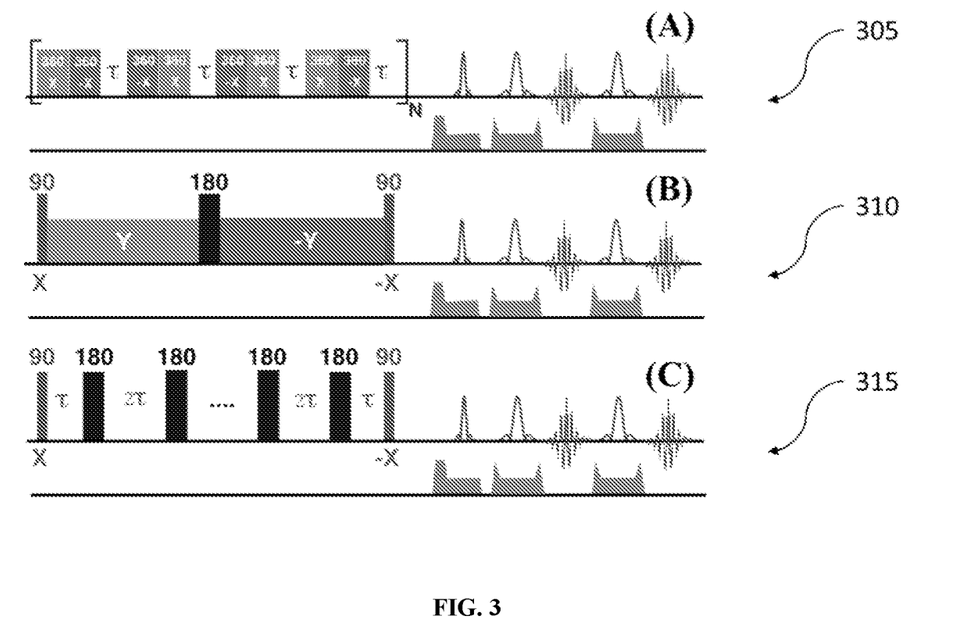
FIG. 3 illustrates embodiments of MRI methods for detecting glucose in CSF.

FIG. 3 illustrates three possible MRI methods for detecting glucose in CSF. In some embodiments illustrated in (a), on-resonance variable delay multiple pulse (onVDMP) 305 is used, which is a train of binomial pulses followed by an image acquisition module. In some embodiments, a simple binomial pulse composed of two high power pulses with alternating phase (pp̄) is used. The phases of the binomial pulse pairs are cycled between each pulse unit (RRR̄R̄) to make the sequence robust against B0/B1 inhomogeneities. τ is the inter-pulse delay or mixing time.

In other embodiments illustrated in (b), a T1rho method 310 is used, in which the water magnetization is first flipped by a hard 90-degree pulse and then locked by a spin-lock pulse. The hard 90-degree pulse following the spin-lock pulse flips the magnetization back to the Z-axis for Mill readout. The 180-degree pulse in the middle of spin-lock pulse is used to improve the robustness to the B0 inhomogeneity. In still other embodiments illustrated in (c), a Carr, Purcell, Meiboom, Gill (CPMG) sequence 315 is used, which is a train of 180-degree pulses with an interval of 2 t applied between two 90-degree pulses. In addition to these, other embodiments use continuous saturation with RF at an OH frequency of the sugar.

EXAMPLES

The following describes some concepts of the current invention with reference to particular embodiments. The general concepts of the current invention are not limited to the examples described.

Example 1

An example embodiment is related to the glucose transporter and glymphatic system in one Alzheimer's disease mouse brain with tau pathology using onVDMP MRI.
Methods
Animals The study was carried out under the approval of Johns Hopkins University animal care and use. Four female Tau4RΔK (Tau) mice (49) with an age of 7-8 months and four female age-matched C57BL/6J mice were used for the AD study. Two age-matched BALB/c mice were used for the validation of glucose uptake using an MRS method. The Tau mice were bred at Johns Hopkins University and the onset of tau tangles starts at the age of six months (49). A catheter was placed in the tail vein for glucose administration before placing the animal in the scanner.
MRI Experiments All MRI experiments were performed on a horizontal bore 11.7 T Bruker Biospec system (Bruker, Ettlingen, Germany) equipped with actively shielded gradients, with a maximum strength of 74 Gauss/cm. A 72 mm quadrature volume resonator was used as a transmitter and a 2×2 mouse phased array coil for acquisition. All animals were anesthetized using 2% isoflurane in medical air, followed by 1% to 1.5% isoflurane for maintenance during the MRI scan. The mouse head was positioned using a bite bar and two ear pins. During the MRI scan, mice were placed on a water-heated animal bed. Respiratory rate was monitored via a pressure sensor (SAII, Stony Brook, NY, USA) and maintained at 40-60 breaths per minute. The $B_0$ field over the mouse brain was adjusted using field-mapping and second-order shimming.

The MRI sequence used for monitoring the glucose uptake in brain and CSF was onVDMP, illustrated in (a) of FIG. 3. The duration of each binomial pulse pair was 3 ms, and the length of a saturation module was proportional to the total number of binomial pulse pairs. Two independent onVDMP sequences with different saturation-module lengths (i.e. 36 ms and 300 ms) were repeated in an interleaved fashion to detect the glucose uptake in brain parenchyma and CSF, respectively. Other imaging parameters were: TR/TE=2.5 s/5 ms, RARE factor=23, slice thickness=1 mm, a matrix size of 196×128 within a FOV of 20×10 mm². The scan time for each onVDMP experiment was fixed to 7.5 s and the dynamic glucose enhanced (DGE) images were acquired continuously for 27.5 min. A bolus of 0.15 mL 50% w/w glucose (0.5 g/mL, clinical-grade dextrose, Hospira, Lake Forest, IL) was given at $10^{th}$ min of the dynamic experiment through the tail vein using a syringe pump (Harvard Apparatus Holliston, MA, USA). The first five minutes of dynamic scan were used as dummy scans to make sure system reached steady-state.

Data Analysis

According to $R_{1\rho}$ theory (50-52), the water signal intensity (S) after applying an onVDMP sequence is expressed in some embodiments as:

$$S = S_0 e^{-T_{onvDMP} R_{1\rho}} \quad (1)$$

where $S_0$ is the water signal intensity without saturation. Because $\Delta R_{1\rho}$ induced by glucose infusion is relatively small (41-43,53,54), the normalized change of water signal intensity $\Delta Z$ is approximated in some embodiments as:

$$\Delta Z = (S_{base} - S)/S_{base} = 1 - e^{-T_{onvDMP} \Delta R_{1\rho}} \approx T_{onvDMP} \Delta R_{1\rho} \quad (2)$$

where $S_{base}$ is the referenced water signal intensity. In this study, the average of water signal intensity before glucose infusion was used as $S_{base}$. The dynamic images are calculated in some embodiments by averaging N images within a certain time period (55):

$$S_{ave} = \Sigma_{n=1}^{N} \Delta Z(n)/N \quad (3)$$

To correct for motion between DGE images, image registration was applied using Medical Imaging Registration Toolbox (MIRT) (56). The regions of interest (ROIs) were selected by hand with the reference to mouse brain atlas (https://mouse.brain-map.org).

The glucose uptake curves measured by DGE MRI are fitted using exponential functions in some embodiments to allow quantitative comparison:

$$\Delta DGE(t) = A_{DGE}(1 - e^{-t/T_{u,DGE}}) \quad (4)$$

where $\Delta DGE(t)$ is the DGE signal difference determined by onVDMP MRI. $T_{u,DGE}$ is the glucose uptake lifetime. The half-life time of glucose uptake was calculated by the equation: $T_{half} = T_u * 0.6931$. $A_{DGE}$ represents the amplitudes of glucose uptake at equilibrium measured by onVDMP. A two-sample t-test was performed on the fitting parameters between the AD and WT groups and was considered statistically significant for P<0.05 and highly significant when P<0.001.

Results and Discussion

DGE Experiments on AD and WT Mice

Figure 4:
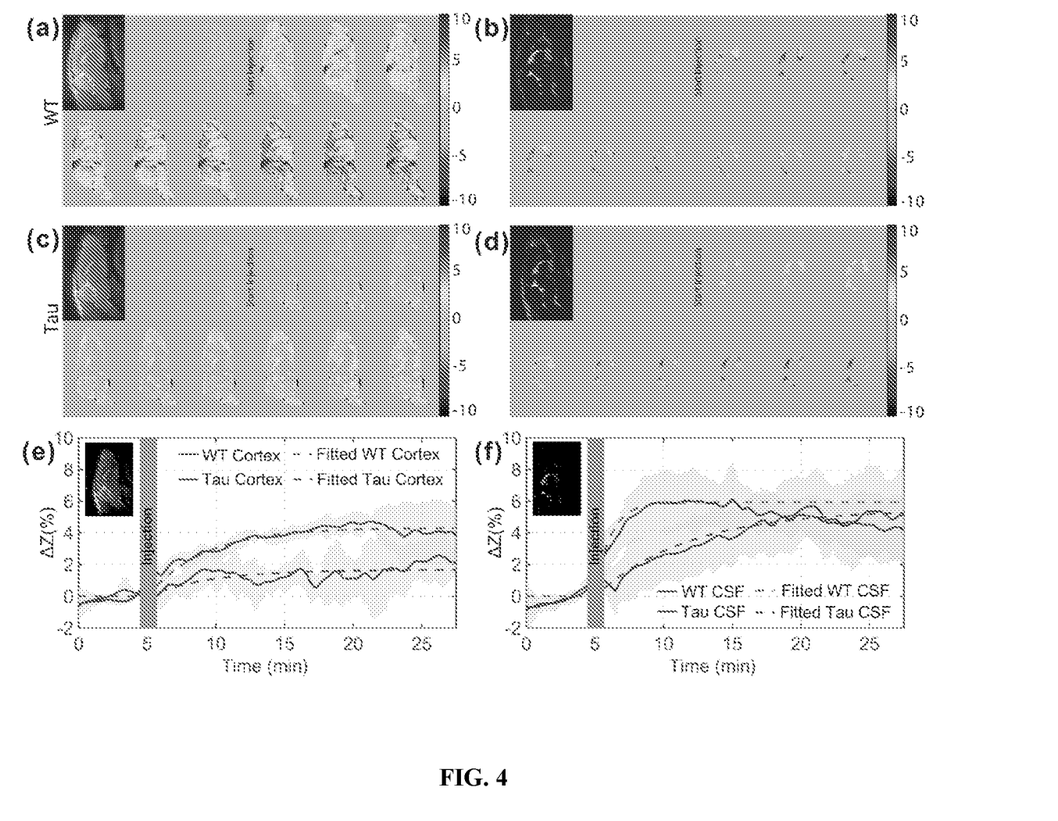
FIG. 4 illustrates dynamic maps for WT and Tau mice for a dynamic glucose enhanced (DGE) experiment, and averaged time-resolved DGE signal difference curves for the cortex and CSF.

FIG. 4 illustrates dynamic maps for WT and Tau mice over a 27.5 min dynamic glucose enhanced (DGE) experiment. The brain tissue maps were recorded using the onVDMP sequence with 12 binomial pulse pairs, while the CSF maps were obtained with 100 binomial pulse pairs. Each dynamic map was calculated by averaging 10 successive DGE images, which lead to a time window of 150 s.

The dynamic maps were utilized to monitor the glucose uptake in mouse brain after infusion. The representative dynamic maps of WT and Tau are shown in (a)-(d). Each dynamic map was calculated by averaging 10 successive DGE images, which corresponds to a time-interval of 150 s.

FIG. 4 also illustrates the averaged time-resolved DGE signal difference curves for the cortex and CSF of WT and Tau mice. The regions of interest (ROIs) used for determining the DGE curves are indicated in the inserted images with red lines. Shaded regions in the graphs represent the standard deviation of the curves (n=4). The averaged DGE curves (solid lines) and the corresponding curves from fitting with Eq. 6 (dotted lines) are shown.

The averaged DGE curves of both WT (n=4) and Tau (n=4) mice for the cortex and CSF are plotted in (e) and (f) respectively. From the dynamic maps and curves, the glucose uptake was slow in the parenchymal ROI (cortex) for both WT and Tau mice, reaching a plateau after about 20 min. By fitting the DGE curves using Eq. 4, the fitted $A_{DGE}$ of WT parenchyma (5.42±0.70%) was clearly larger than that of Tau parenchyma (1.70±1.33%, p=0.005). The uptake half-life time of parenchyma was 4.71±1.03 min for WT mice and not significantly different for Tau mice (5.14±0.30 min, p=0.511). The DGE signal of WT CSF built up quickly after glucose infusion and plateaued around 10 min. The uptake half-life time of WT CSF was 1.24±0.24 min. Interestingly, after reaching a plateau, the DGE signal of WT CSF began to decay, as can be seen in both dynamic maps and DGE curves. The DGE signal of CSF in Tau-mice kept increasing after glucose infusion and reached a plateau only around 25 min with a half-life time of 7.80±1.14 min, which is significantly longer than WT (p<0.001). The CSF $A_{DGE}$ values were similar between WT mice ($A_{DGE}$=7.03±2.12%) and Tau mice ($A_{DGE}$=6.72±2.22%, p=0.871).

The DGE curves obtained by onVDMP on brain tissue of WT mice showed a similar pattern to those acquired on both human (43,54) and animal brain (41,53,57) using the $T_{1\rho}$ method, i.e., the DGE curves build up in the first 10-15 minutes after glucose infusion and then decay slowly. The half-life time of glucose uptake obtained by the onVDMP method (4.71±1.18 min) is consistent with that measured by MRS (4.16±0.69 min) and previous $^{13}$C MRS measurements (5.10±0.11 min) (28), which suggests that the change of onVDMP signal is correlated with the glucose concentration in brain. Glucose also induces $T_2$ relaxation change due to the chemical exchanging between glucose hydroxy protons and water (58,59), and this $T_2$ relaxation change also contributes to the change of onVDMP signal as indicated in Eqs. 2 and 3, which is similar to the $T_{1\rho}$ based methods.

The glucose uptake in brain is related to the glucose delivery, transport and metabolism functions. From the results shown in (a), (c), (e) of FIG. 4, the glucose uptake in the cortex of Tau mice is significantly reduced compared to that of WT mice (signal intensities of 1.6±1.3% v.s. 4.3±1.3%, p=0.016). This is consistent with the observation that the glucose uptake is impaired in AD brain due to the reductions of both GLUT1 and GLUT3 expression at the BBB (21,60,61). Few studies have been performed to measure glucose uptake in brain CSF (62). In the current study, an onVDMP sequence with a long saturation module was employed to suppress the parenchymal signal, enhancing the detection sensitivity of CSF. Notice that such an approach would not work for MRS, as the $T_2$ of the glucose protons is short, but here the water signal in CSF is being studied. The buildup process of the DGE curve in CSF is again related to the glucose delivery and transport at the BCSFB. From the dynamic maps and curve in (b), (d), (f) of FIG. 4, Tau mouse CSF has much slower glucose uptake compared to the WT mouse CSF, which, assuming similar delivery, suggests that the glucose transporter at the BCSFB is also impaired in the AD brain. From previous studies, glucose is alternatively redistributed to brain parenchyma through a CSF and interstitial fluid (ISF) exchanging process, i.e. the glymphatic pathway (FIG. 2), (63,64) and the glymphatic pathway of AD brain has been reported to be dysfunctional (6). This may explain the observation that the DGE signal of WT CSF began to decay after reaching a maximum around 15 minutes, while the DGE signal of Tau CSF kept increasing. For WT mice, the DGE signal at 27.5 minutes dropped about 1.5±0.5% from the peak value 6±0.3% while the glucose level in blood barely decreased in 12.5 minutes as demonstrated in a previous study (65), which supports the standpoint that glymphatic pathway plays a role for glucose transport into brain (63). The evidence shown in this study suggests that glucose as a natural biodegradable contrast agent has the potential to be a non-invasive method to detect CSF-ISF exchange and reveal the function of glymphatic system.

Example 2

An example embodiment is related to altered glucose uptake and clearance in the APP/PS1 Alzheimer's mouse brain detected by dynamic glucose enhanced (DGE) MRI at 3 T.

Methods

Animal Preparation

All animal experiments were approved by the Animal Ethics Committee and followed the institutional guidelines of Institutional Laboratory Animal Research Unit of City University of Hong Kong. Ten AD mice (APP/PS1, five with age of 6 months (6M) and five with age of 16 months (16M), male, Jackson Laboratory, Maine) and ten age-matched WT mice (C57, male, Jackson Laboratory, Maine) were used to study the cerebral glucose uptake and clearance in AD. APP/PS1 mice are double transgenic mice expressing a chimeric mouse/human amyloid precursor protein (Mo/HuAPP695swe) and a mutant human presenilin 1 (PS1-dE9), both directed to CNS neurons. Both mutations are associated with early-onset AD. Another six 6M WT mice were used for the control experiments.

MRI Experiments

The onVDMP sequence diagram is shown in (a) of FIG. 3. By setting a different binomial pulse number N, the saturation length is adjusted to image the parenchyma and CSF, respectively. In this study, the saturation length was set to 60 ms for imaging parenchyma and 900 ms for imaging CSF. DGE experiments on both parenchyma and CSF images are acquired in an alternate way in some embodiments during one acquisition, similar to the experiments in example 1.

When carrying out the MRI experiments on mice, anesthesia was induced and maintained using isoflurane at 2% and 1.5%, respectively. The isoflurane was mixed with 90% oxygen generated by an oxygen concentrator. The flow rate of oxygen generator was set to 2 liter per minute (LPM) and kept unchanged during the whole experiment. Mice were placed in a horizontal bore 3 T Bruker BioSpec animal scanner (Bruker, Germany). A 82-mm-diameter quadrature coil and a 23-mm-diameter mouse brain surface coil were used for transmitting and receiving signal, respectively. A catheter was placed in the tail vein for glucose administration before placing the animal in the scanner. A bolus of 0.15 mL filtered 50% D-glucose was injected into the mouse body through the tail vein over one minute (speed: 0.15 ml/min) using a MRI-compatible syringe pump (Harvard Apparatus). Mouse body temperature was maintained at 37° C. using a warming pad. Respiration and body temperature were continuously monitored using an MRI-compatible monitor system (SA Instruments, Inc). Before DGE acquisition, the $B_0$ field over the mouse brain was shimmed using field-mapping and second-order shimming. The read-out module was rapid acquisition with refocused echoes (RARE) with TR/TE=2.5 s/4.7 ms, RARE factor=32, centric encoding, slice thickness=2 mm, a matrix size of 96×96 within a field of view (FOV) of 20×20 mm$^2$, resulting in a time resolution of 15 s for each pair of images (7.5 s for parenchyma and 7.5 s for CSF). A total number of 550 images were acquire for each DGE module, thus leading to a total scanning time of 1 h 8 min 45 s. The glucose injection was started at 8 min 45 s and lasted for 1 min. The first 10 images, which did not reach the steady state, were discarded during processing. Hence the baseline is 7 min 30 s (30 parenchyma images and 30 CSF images), and the monitoring time after glucose injection is 1 h (240 parenchyma images and 240 CSF images). The image slice was positioned based on a collected sagittal image of the mouse brain with the position of the coronal image slice set to −1.4 mm with respect to the anterior commissure (AC).

Data Analysis

All image processing and data analyses were performed using custom written code in MATLAB (R2018b, MathWorks, USA). When calculating DGE kinetic curves, baseline signal $S_{base}$ was generated by averaging the 30 baseline images. Since the total number of DGE images was large (270 for each mouse), every set of 15 images were averaged to visualize the dynamic process of glucose changes. Then Eq. 5 was used for each time point to construct the DGE kinetic curves after glucose administration.

$$\Delta S(A) = \frac{S_{base} - s(t)}{S_{base}} \quad (5)$$

The DGE data of CSF were fitted by a simple gamma variate model(66,67) for only the first 20 mins after glucose injection, giving an uptake rate and an estimate of the initial rate of clearance:

$$\Delta S'_{CSF}(t) = A(t - t_0)^{\frac{1}{\mu_{in}}} e^{-\mu_{out}(t - t_0)} \quad (6)$$

where A is an amplitude modulation parameter, $\mu_{in}$ represents the glucose uptake rate, $\mu_{out}$ represents the initial rate of clearance. This dynamic equation is different from Eq. 4, while Eq. 4 is suitable for extremely slow uptake case as demonstrated in the Tau AD mouse model. The maximum signal that CSF DGE reached is directly extracted in some embodiments after fitting as $S_{max}=\max(\Delta S'_{CSF}(t))$. For both parenchymal and CSF DGE curves, fitting was achieved using the built-in nonlinear least-squares curve fitting function in MATLAB. When doing the statistical analysis, comparisons were made between groups of mice using the Student's t-test. Differences were regarded as significant for a P-value<0.05.

Results and Discussion

CSF DGE Results for WT and APP/PS1 Mice

Figure 5:
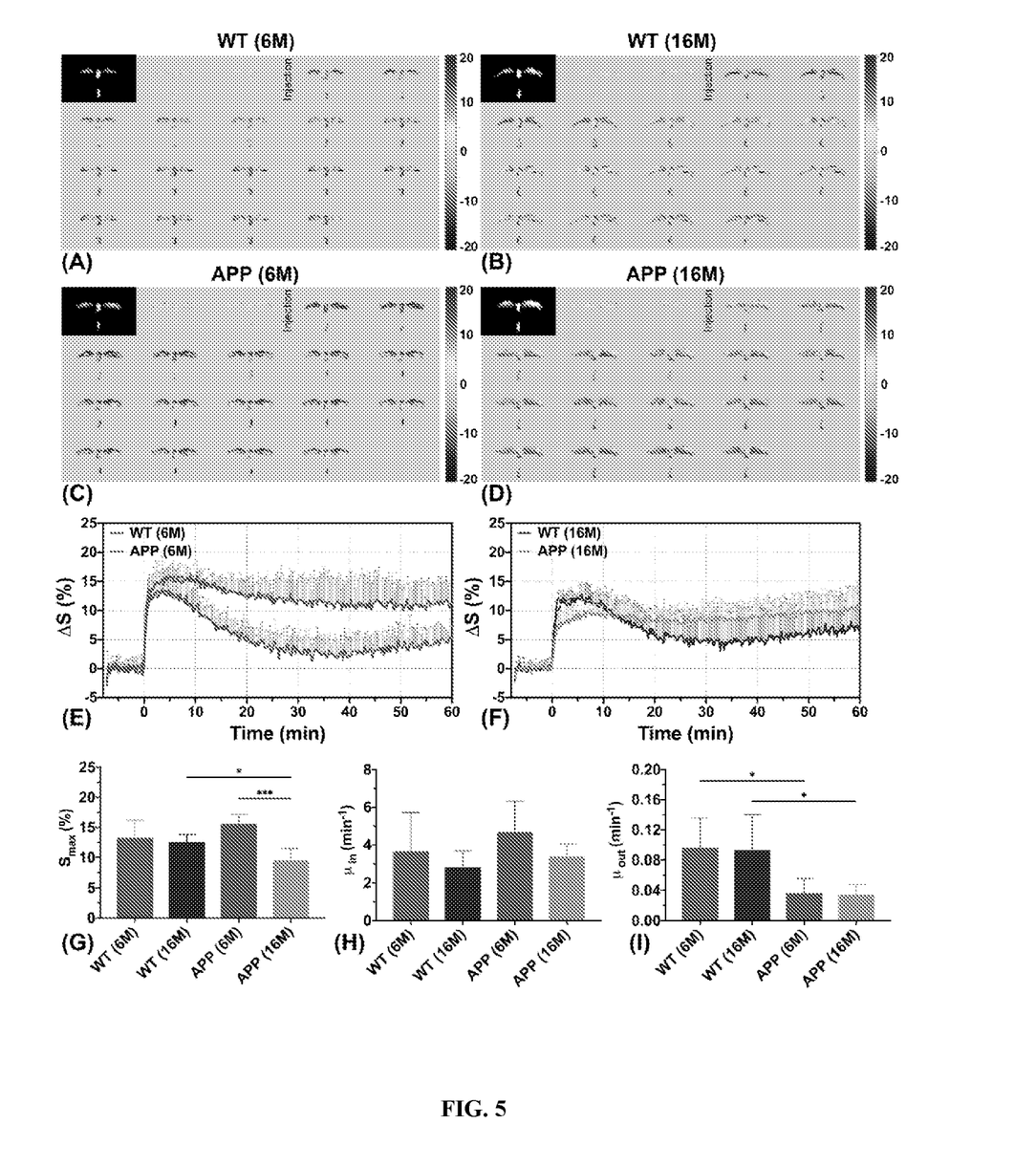
FIG. 5 shows DGE MRI results for CSF of WT and APP/PS1 mice.

FIG. 5 shows DGE MRI results for CSF of WT and APP/PS1 mice. Dynamic difference images before and after infusion for WT mice are shown in (A) and (B) and for APP/PS1 mice in (C) and (D). In addition, (A) and (C) show results at 6 months (6M) and (B) and (D) show results at 16 months (16M). DGE images were averaged over sets of 15 for display (18 out of 270). In (E), experimental (solid line) and fitted (dashed line) CSF DGE signal difference curves are shown for WT (6M, n=5) and APP/PS1 (6M, n=5) mice, while in (F) experimental (solid line) and fitted (dashed line) CSF DGE signal difference curves are shown for WT (16M, n=5) and APP/PS1 (16M, n=5) mice. In (G)-(I), the figure shows a comparison of fitted uptake and clearance parameters $S_{max}$ (g), $\mu_{in}$ (h) $\mu_{out}$ (i) between WT and APP/PS1 mice for two age groups (6M and 16M). Significance levels were: *, p<0.05; , p<0.01; *, p<0.001.

The DGE images for CSF of young (6M) and old groups (16M) are shown in (A)-(D) of FIG. 5. The CSF DGE time courses for the WT and APP/PS1 mice are plotted in (E) and (F), providing detailed dynamic information about the glucose uptake and clearance. In (E) it can be seen that the D-glucose uptake in CSF initially was comparable in the two groups of young mice (ΔS at 2 min: 14.56±2.86% in WT vs 12.70±2.30% in APP/PS1, P=0.291), while the washout phase of WT was obviously faster than that of APP/PS1 (ΔS at 30 min: 3.18±2.95% vs 11.84±4.13%, P=0.005). In the two old groups, the curves of D-glucose in CSF in both WT and APP/PS1 (F) visually resemble the corresponding young groups, except for three features: (i) a somewhat longer plateau for the WT mice, (ii) a reduced initial ΔS for the APP/PS1 mice, and (iii) negligible ΔS difference between the 5 min and 60 min time points for APP/PS1. In order to estimate quantitative parameters describing the uptake and clearance, a fit to several mathematical models was tried. None could fit the whole CSF curve accurately, but using a gamma-variate model (see Eq. 6) with three unknowns ($S_{max}$, $\mu_{in}$, $\mu_{out}$), it was possible to closely fit the uptake and get an initial rate estimate ($\mu_{out}$) for the clearance by fitting only the first 20 min post-infusion. These estimated uptake and clearance parameters are shown in (G)-(I). The $S_{max}$ for APP/PS1 mice was close to that of WT at 6M (P=0.156), but became significantly lower at 16M (P=0.019). There was a significant decrease of $S_{max}$ for APP/PS1 mice at 16M compared to 6M (P<0.001), indicating a clear age dependence. There was no significant difference in D-glucose uptake rate $\mu_{in}$ between WT and APP/PS1 mice either in young or old mouse groups (H). The $\mu_{in}$ appeared to decrease slightly for both WT or APP/PS1 mice during aging, but this did not reach significance (P=0.425 for WT and P=0.141 for APP/PS1). For the washout initial rates of D-glucose in CSF, $\mu_{out}$ was significantly slower in APP/PS1 compared to WT at both 6M (P=0.017) and 16M (P=0.031). This indicates that D-glucose clearance becomes slower in APP/PS1 mice compared to age-matched WT mice.

From FIG. 5, the DGE CSF curves showed a fast uptake for all groups followed by slow clearance for three groups and negligible clearance for the old APP/PS1 group. An accurate mathematical model was not found to describe these full curves. However to obtain a first quantitative estimate of the rate differences of glucose uptake and clearance between AD and WT mice, the DGE CSF curves were fitted for the first 20 min only using a gamma-variate model that provided a $S_{max}$(CSF), an uptake rate $\mu_{in}$ (CSF), and an initial rate for clearance, $\mu_{out}$ (CSF). The gamma variate model has been applied previously to describe vascular input functions in dynamic contrast enhanced (DCE) and dynamic susceptibility-contrast (DSC) MRI. (66,67) In those particular applications for determining perfusion parameters, the kinetics for tracer concentrations of the agent show a fast uptake and clearance. However, the gamma-variate function is just a mathematical description for an initial signal rise followed by an exponential decay (Eq. 6). The gamma-variate function was suitable to closely fit the D-glucose uptake in CSF and to obtain an estimate for the initial rate for signal changes following the plateau. If there would be no clearance, this would give a zero rate, while a continuing increase would give a negative $\mu_{out}$, so this is mathematically straightforward and can describe the possible physiological conditions. For the D-glucose uptake in CSF ($S_{max}$), significant changes were not found (P=0.156, from (G) in FIG. 5) between WT and APP/PS1 mice for the 6M group, but for the 16M APP/PS1 group, a significantly lower D-glucose uptake was found for APP/PS1 mice compared to the 16M WT mice (from (G) in FIG. 5). While the D-glucose uptake rate μm for CSF did not differ between groups (from (H) in FIG. 5), the clearance rate was slower in both young and old APP/PS1 mice (from (I) in FIG. 5), compared to WT. The clearance of the D-glucose from CSF could be related to the glymphatic system, which is a paravascular route for cerebrospinal fluid (CSF) flow through the brain parenchyma(6). After entering the CSF through the blood-cerebrospinal fluid barrier (BCSFB), D-glucose is recirculated to the parenchyma through the glymphatic pathway (FIG. 2) (68). The significantly reduced CSF clearance rates $\mu_{out}$ for 6M and 16M APP mice are consistent with the recent findings that the CSF clearance rate is much smaller in AD mice(63,69). This reduced CSF clearance detected by DGE could serve as an imaging biomarker to indicate early neuropathology in AD, especially with its distinctive features apart from normal aging as shown in age-matched WT (6M, 16M).

CONCLUSIONS

In both AD studies, it was demonstrated that glucose is usable as one biodegradable tracer for the monitoring the glucose uptake in both mouse brains and CSF as well as for assessing the brain lymphatic function on both high and low MRI fields. The results suggest that use of D-glucose as a natural biodegradable contrast agent for MRI has the potential to be a non-invasive method to reveal altered glucose uptake, utilization in both early and late stage of AD, together with altered functioning of glymphatic system for D-glucose clearance.

The above provides examples according to particular embodiments of the current invention. The broad concepts of the current invention are not limited to only those particular examples.

The term "computer" is intended to have a broad meaning that may be used in computing devices such as, e.g., but not limited to, standalone or client or server devices. The computer may be, e.g., (but not limited to) a personal computer (PC) system running an operating system such as, e.g., (but not limited to) MICROSOFT® WINDOWS® NT/98/2000/XP/Vista/Windows 7/8/etc. available from MICROSOFT® Corporation of Redmond, Wash., U.S.A. or an Apple computer executing MAC® OS from Apple® of Cupertino, Calif., U.S.A. However, the invention is not limited to these platforms. Instead, the invention may be implemented on any appropriate computer system running any appropriate operating system. In one illustrative embodiment, the present invention may be implemented on a computer system operating as discussed herein. The computer system may include, e.g., but is not limited to, a main memory, random access memory (RAM), and a secondary memory, etc. Main memory, random access memory (RAM), and a secondary memory, etc., may be a computer-readable medium that may be configured to store instructions configured to implement one or more embodiments and may comprise a random-access memory (RAM) that may include RAM devices, such as Dynamic RAM (DRAM) devices, flash memory devices, Static RAM (SRAM) devices, etc.

The secondary memory may include, for example, (but is not limited to) a hard disk drive and/or a removable storage drive, representing a floppy diskette drive, a magnetic tape drive, an optical disk drive, a compact disk drive CD-ROM, flash memory, etc. The removable storage drive may, e.g., but is not limited to, read from and/or write to a removable storage unit in a well-known manner. The removable storage unit, also called a program storage device or a computer program product, may represent, e.g., but is not limited to, a floppy disk, magnetic tape, optical disk, compact disk, etc. which may be read from and written to the removable storage drive. As will be appreciated, the removable storage unit may include a computer usable storage medium having stored therein computer software and/or data.

In alternative illustrative embodiments, the secondary memory may include other similar devices for allowing computer programs or other instructions to be loaded into the computer system. Such devices may include, for example, a removable storage unit and an interface. Examples of such may include a program cartridge and cartridge interface (such as, e.g., but not limited to, those found in video game devices), a removable memory chip (such as, e.g., but not limited to, an erasable programmable read only memory (EPROM), or programmable read only memory (PROM) and associated socket, and other removable storage units and interfaces, which may allow software and data to be transferred from the removable storage unit to the computer system.

The computer may also include an input device may include any mechanism or combination of mechanisms that may permit information to be input into the computer system from, e.g., a user. The input device may include logic configured to receive information for the computer system from, e.g. a user. Examples of the input device may include, e.g., but not limited to, a mouse, pen-based pointing device, or other pointing device such as a digitizer, a touch sensitive display device, and/or a keyboard or other data entry device (none of which are labeled). Other input devices may include, e.g., but not limited to, a biometric input device, a video source, an audio source, a microphone, a web cam, a video camera, and/or other camera. The input device may communicate with a processor either wired or wirelessly.

The computer may also include output devices which may include any mechanism or combination of mechanisms that may output information from a computer system. An output device may include logic configured to output information from the computer system. Embodiments of output device may include, e.g., but not limited to, display, and display interface, including displays, printers, speakers, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), etc. The computer may include input/output (I/O) devices such as, e.g., (but not limited to) communications interface, cable and communications path, etc. These devices may include, e.g., but are not limited to, a network interface card, and/or modems. The output device may communicate with processor either wired or wirelessly. A communications interface may allow software and data to be transferred between the computer system and external devices.

The term "data processor" is intended to have a broad meaning that includes one or more processors, such as, e.g., but not limited to, local processors or processors that are connected to a communication infrastructure (e.g., but not limited to, a communications bus, cross-over bar, interconnect, or network, etc.). The term data processor may include any type of processor, microprocessor and/or processing logic that may interpret and execute instructions (e.g., for example, a field programmable gate array (FPGA)). The data processor may comprise a single device (e.g., for example, a single core) and/or a group of devices (e.g., multi-core). The data processor may include logic configured to execute computer-executable instructions configured to implement one or more embodiments. The instructions may reside in main memory or secondary memory. The data processor may also include multiple independent cores, such as a dual-core processor or a multi-core processor. The data processors may also include one or more graphics processing units (GPU) which may be in the form of a dedicated graphics card, an integrated graphics solution, and/or a hybrid graphics solution. The data processor may be onboard, external to other components, or both. Various illustrative software embodiments may be described in terms of this illustrative computer system. After reading this description, it will become apparent to a person skilled in the relevant art(s) how to implement the invention using other computer systems and/or architectures.

The term "data storage device" is intended to have a broad meaning that includes removable storage drive, a hard disk installed in hard disk drive, flash memories, removable discs, non-removable discs, etc. In addition, it should be noted that various electromagnetic radiation, such as wireless communication, electrical communication carried over an electrically conductive wire (e.g., but not limited to twisted pair, CAT5, etc.) or an optical medium (e.g., but not limited to, optical fiber) and the like may be encoded to carry computer-executable instructions and/or computer data that embodiments of the invention on e.g., a communication network. These computer program products may provide software to the computer system. It should be noted that a computer-readable medium that comprises computer-executable instructions for execution in a processor may be configured to store various embodiments of the present invention.

REFERENCES

1. Iliff J J, Wang M, Liao Y, Plogg B A, Peng W, Gundersen G A, Benveniste H, Vates G E, Deane R, Goldman S A, Nagelhus E A, Nedergaard M. A paravascular pathway facilitates CSF flow through the brain parenchyma and the clearance of interstitial solutes, including amyloid beta. Sci Transl Med 2012; 4(147):147ra111.
2. Xu Z, Xiao N, Chen Y, Huang H, Marshall C, Gao J, Cai Z, Wu T, Hu G, Xiao M. Deletion of aquaporin-4 in APP/PS1 mice exacerbates brain Abeta accumulation and memory deficits. Mol Neurodegener 2015; 10:58.
3. Xie L, Kang H, Xu Q, Chen M J, Liao Y, Thiyagarajan M, O'Donnell J, Christensen D J, Nicholson C, Iliff J J, Takano T, Deane R, Nedergaard M. Sleep drives metabolite clearance from the adult brain. Science 2013; 342 (6156):373-377.
4. Rasmussen M K, Mestre H, Nedergaard M. The glymphatic pathway in neurological disorders. The Lancet Neurology 2018; 17(11):1016-1024.
5. Louveau A, Da Mesquita S, Kipnis J. Lymphatics in Neurological Disorders: A Neuro-Lympho-Vascular Component of Multiple Sclerosis and Alzheimer's Disease? Neuron 2016; 91(5):957-973.

6. Da Mesquita S, Louveau A, Vaccari A, Smirnov I, Cornelison R C, Kingsmore K M, Contarino C, Onengut-Gumuscu S, Farber E, Raper D, Viar K E, Powell R D, Baker W, Dabhi N, Bai R, Cao R, Hu S, Rich S S, Munson J M, Lopes M B, Overall C C, Acton S T, Kipnis J. Functional aspects of meningeal lymphatics in ageing and Alzheimer's disease. Nature 2018; 560(7717):185-191.
7. Absinta M, Ha S K, Nair G, Sati P, Luciano N J, Palisoc M, Louveau A, Zaghloul K A, Pittaluga S, Kipnis J, Reich D S. Human and nonhuman primate meninges harbor lymphatic vessels that can be visualized noninvasively by MRI. Elife 2017; 6.
8. Harrison I F, Siow B, Akilo A B, Evans P G, Ismail O, Ohene Y, Nahavandi P, Thomas D L, Lythgoe M F, Wells J A. Non-invasive imaging of CSF-mediated brain clearance pathways via assessment of perivascular fluid movement with diffusion tensor MRI. Elife 2018; 7.
9. Taoka T, Masutani Y, Kawai H, Nakane T, Matsuoka K, Yasuno F, Kishimoto T, Naganawa S. Evaluation of glymphatic system activity with the diffusion MR technique: diffusion tensor image analysis along the perivascular space (DTI-ALPS) in Alzheimer's disease cases. Jpn J Radiol 2017; 35(4):172-178.
10. Ohene Y, Harrison I F, Nahavandi P, Ismail O, Bird E V, Ottersen O P, Nagelhus E A, Thomas D L, Lythgoe M F, Wells J A. Non-invasive MRI of brain clearance pathways using multiple echo time arterial spin labelling: an aquaporin-4 study. Neuroimage 2019; 188:515-523.
11. Kuo P H, Stuehm C, Squire S, Johnson K. Meningeal Lymphatic Vessel Flow Runs Countercurrent to Venous Flow in the Superior Sagittal Sinus of the Human Brain. Tomography 2018; 4(3):99-104.
12. Iliff J J, Lee H, Yu M, Feng T, Logan J, Nedergaard M, Benveniste H. Brain-wide pathway for waste clearance captured by contrast-enhanced MRI. J Clin Invest 2013; 123(3):1299-1309.
13. Gaberel T, Gakuba C, Goulay R, Martinez De Lizarrondo S, Hanouz J L, Emery E, Touze E, Vivien D, Gauberti M. Impaired glymphatic perfusion after strokes revealed by contrast-enhanced MRI: a new target for fibrinolysis? Stroke 2014; 45(10):3092-3096.
14. Lee H, Mortensen K, Sanggaard S, Koch P, Brunner H, Quistorff B, Nedergaard M, Benveniste H. Quantitative Gd-DOTA uptake from cerebrospinal fluid into rat brain using 3D VFA-SPGR at 9.4 T. Magn Reson Med 2018; 79(3):1568-1578.
15. Ringstad G, Valnes L M, Dale A M, Pripp A H, Vatnehol S S, Emblem K E, Mardal K A, Eide P K. Brain-wide glymphatic enhancement and clearance in humans assessed with MRI. JCI Insight 2018; 3(13).
16. Eide P K, Ringstad G. MRI with intrathecal MRI gadolinium contrast medium administration: a possible method to assess glymphatic function in human brain. Acta Radiol Open 2015; 4(11):2058460115609635.
17. Ringstad G, Vatnehol SAS, Eide P K. Glymphatic MRI in idiopathic normal pressure hydrocephalus. Brain 2017; 140(10):2691-2705.
18. Taoka T, Naganawa S. Gadolinium-based Contrast Media, Cerebrospinal Fluid and the Glymphatic System: Possible Mechanisms for the Deposition of Gadolinium in the Brain. Magn Reson Med Sci 2018; 17(2):111-119.
19. McDonald R J, McDonald J S, Kallmes D F, Jentoft M E, Murray D L, Thielen K R, Williamson E E, Eckel L J. Intracranial Gadolinium Deposition after Contrast-enhanced MR Imaging. Radiology 2015; 275(3):772-782.
20. Iliff J J, Wang M, Liao Y, Plogg B A, Peng W, Gundersen G A, Benveniste H, Vates G E, Deane R, Goldman S A. A paravascular pathway facilitates CSF flow through the brain parenchyma and the clearance of interstitial solutes, including amyloid β. Science translational medicine 2012; 4(147):147ra111-147ra111.
21. Simpson I A, Chundu K R, Davies-Hill T, Honer W G, Davies P. Decreased concentrations of GLUT1 and GLUT3 glucose transporters in the brains of patients with Alzheimer's disease. Ann Neurol 1994; 35(5):546-551.
22. Mooradian A D, Chung H C, Shah G N. GLUT-1 expression in the cerebra of patients with Alzheimer's disease. Neurobiol Aging 1997; 18(5):469-474.
23. Nordberg A, Rinne J O, Kadir A, Långström B. The use of PET in Alzheimer disease. Nature Reviews Neurology 2010; 6(2):78.
24. Kato T, Inui Y, Nakamura A, Ito K. Brain fluorodeoxyglucose (FDG) PET in dementia. Ageing research reviews 2016; 30:73-84.
25. Schwartz W J, Smith C B, Davidsen L, Savaki H, Sokoloff L, Mata M, Fink D J, Gainer H. Metabolic mapping of functional activity in the hypothalamo-neurohypophysial system of the rat. Science 1979; 205 (4407):723-725.
26. Phelps M E, Mazziotta J C, Huang S C. Study of cerebral function with positron computed tomography. J Cereb Blood Flow Metab 1982; 2(2):113-162.
27. van Zijl P C, Chesnick A S, DesPres D, Moonen C T, Ruiz-Cabello J, van Gelderen P. In vivo proton spectroscopy and spectroscopic imaging of [1-13C]-glucose and its metabolic products. Magn Reson Med 1993; 30(5): 544-551.
28. Van Zijl P C, Davis D, Eleff S M, Moonen C T, Parker R J, Strong J M. Determination of cerebral glucose transport and metabolic kinetics by dynamic MR spectroscopy. Am J Physiol 1997; 273(6 Pt 1):E1216-1227.
29. Xin L, Lanz B, Lei H, Gruetter R. Assessment of metabolic fluxes in the mouse brain in vivo using 1H-[13C] NMR spectroscopy at 14.1 Tesla. J Cereb Blood Flow Metab 2015; 35(5):759-765.
30. Mason G F, Rothman D L, Behar K L, Shulman R G. NMR determination of the TCA cycle rate and alpha-ketoglutarate/glutamate exchange rate in rat brain. J Cereb Blood Flow Metab 1992; 12(3):434-447.
31. Gruetter R, Adriany G, Merkle H, Anderson P M. Broadband decoupled, H-1 localized C-13 MRS of the human brain at 4 tesla (vol 36, pg 659, 1996). Magn Reson Med 1997; 37(2):267-267.
32. de Graaf R A, Mason G F, Patel A B, Behar K L, Rothman D L. In vivo 1H-[13C]-NMR spectroscopy of cerebral metabolism. NMR Biomed 2003; 16(6-7):339-357.
33. Henry P G, Adriany G, Deelchand D, Gruetter R, Marjanska M, Oz G, Seaquist E R, Shestov A, Ugurbil K. In vivo 13C NMR spectroscopy and metabolic modeling in the brain: a practical perspective. Magn Reson Imaging 2006; 24(4):527-539.
34. Nabuurs C I, Klomp D W, Veltien A, Kan H E, Heerschap A. Localized sensitivity enhanced in vivo 13C MRS to detect glucose metabolism in the mouse brain. Magn Reson Med 2008; 59(3):626-630.
35. Du F, Zhang Y, Zhu X H, Chen W. Simultaneous measurement of glucose blood-brain transport constants and metabolic rate in rat brain using in-vivo H-1 MRS. J Cerebr Blood F Met 2012; 32(9):1778-1787.
36. Gruetter R, Novotny E J, Boulware S D, Rothman D L, Shulman R G. 1H NMR studies of glucose transport in the human brain. J Cereb Blood Flow Metab 1996; 16(3): 427-438.

37. De Feyter H M, Behar K L, Corbin Z A, Fulbright R K, Brown P B, McIntyre S, Nixon T W, Rothman D L, de Graaf R A. Deuterium metabolic imaging (DMI) for MRI-based 3D mapping of metabolism in vivo. Sci Adv 2018; 4(8): eaat7314.
38. Chan K W, McMahon M T, Kato Y, Liu G, Bulte J W, Bhujwalla Z M, Artemov D, Van Zijl P C. Natural D-glucose as a biodegradable MRI contrast agent for detecting cancer. Magn Reson Med 2012; 68(6):1764-1773.
39. Walker-Samuel S, Ramasawmy R, Torrealdea F, Rega M, Rajkumar V, Johnson S P, Richardson S, Gonçalves M, Parkes H G, Arstad E. In vivo imaging of glucose uptake and metabolism in tumors. Nat Med 2013; 19(8):1067.
40. Yadav N N, Xu J, Bar-Shir A, Qin Q, Chan K W, Grgac K, Li W, McMahon M T, van Zijl P C. Natural D-glucose as a biodegradable MRI relaxation agent. Magn Reson Med 2014; 72(3):823-828.
41. Jin T, Mehrens H, Hendrich K S, Kim S G. Mapping brain glucose uptake with chemical exchange-sensitive spin-lock magnetic resonance imaging. J Cereb Blood Flow Metab 2014; 34(8):1402-1410.
42. Jin T, Mehrens H, Wang P, Kim S G. Chemical exchange-sensitive spin-lock MRI of glucose analog 3-O-methyl-d-glucose in normal and ischemic brain. J Cereb Blood Flow Metab 2018; 38(5):869-880.
43. Paech D, Schuenke P, Koehler C, Windschuh J, Mundiyanapurath S, Bickelhaupt S, Bonekamp D, Baumer P, Bachert P, Ladd M E, Bendszus M, Wick W, Unterberg A, Schlemmer H P, Zaiss M, Radbruch A. T1rho-weighted Dynamic Glucose-enhanced MR Imaging in the Human Brain. Radiology 2017:162351.
44. Xu J, Chan K W, Xu X, Yadav N, Liu G, van Zijl P C. On-resonance variable delay multipulse scheme for imaging of fast-exchanging protons and semisolid macromolecules. Magn Reson Med 2017; 77(2):730-739.
45. Xu X, Chan K W C, Liu H, Li Y, Liu G, C. M. van Zijl P, Xu J. On Resonance VDMP Technique for Improved glucoCEST Detection in Brain Tumors. 2016; Singapore. Proceedings of the 24th Annual Meeting of ISMRM. p 1515.
46. Wu D, Xu J, Lei J, McLane M, van Zijl P C, Burd I. Dynamic glucose enhanced MRI of the placenta in a mouse model of intrauterine inflammation. Placenta
47. Chen L, Barker P B, Weiss R G, van Zijl P C M, Xu J. Creatine and phosphocreatine mapping of mouse skeletal muscle by a polynomial and Lorentzian line-shape fitting CEST method. Magn Reson Med 2019; 81(1):69-78.
48. Chen L, Zeng H, Xu X, Yadav N N, Cai S, Puts N A, Barker P B, Li T, Weiss R G, van Zijl P C M, Xu J. Investigation of the contribution of total creatine to the CEST Z-spectrum of brain using a knockout mouse model. NMR Biomed 2017; 30(12):e3834.
49. Li T, Braunstein K E, Zhang J, Lau A, Sibener L, Deeble C, Wong P C. The neuritic plaque facilitates pathological conversion of tau in an Alzheimer's disease mouse model. Nat Commun 2016; 7:12082.
50. Trott O, Palmer A G. R 1ρ relaxation outside of the fast-exchange limit. J Magn Reson 2002; 154(1):157-160.
51. Trott O, Palmer A G, 3rd. Theoretical study of R(1rho) rotating-frame and R2 free-precession relaxation in the presence of n-site chemical exchange. J Magn Reson 2004; 170(1): 104-112.
52. Jin T, Autio J, Obata T, Kim S G. Spin-locking versus chemical exchange saturation transfer MRI for investigating chemical exchange process between water and labile metabolite protons. Magn Reson Med 2011; 65(5): 1448-1460.
53. Jin T, Iordanova B, Hitchens T K, Modo M, Wang P, Mehrens H, Kim S G. Chemical exchange-sensitive spin-lock (CESL) MRI of glucose and analogs in brain tumors. Magn Reson Med 2018; 80(2):488-495.
54. Schuenke P, Koehler C, Korzowski A, Windschuh J, Bachert P, Ladd M E, Mundiyanapurath S, Paech D, Bickelhaupt S, Bonekamp D, Schlemmer H P, Radbruch A, Zaiss M. Adiabatically prepared spin-lock approach for T1rho-based dynamic glucose enhanced MRI at ultrahigh fields. Magn Reson Med 2017; 78(1):215-225.
55. Xu X, Chan K W, Knutsson L, Artemov D, Xu J, Liu G, Kato Y, Lal B, Laterra J, McMahon M T. Dynamic glucose enhanced (DGE) MRI for combined imaging of blood-brain barrier break down and increased blood volume in brain cancer. Magn Reson Med 2015; 74(6):1556-1563.
56. Myronenko A, Song X. Intensity-based image registration by minimizing residual complexity. IEEE Trans Med Imaging 2010; 29(11):1882-1891.
57. Zu Z, Spear J, Li H, Xu J, Gore J C. Measurement of regional cerebral glucose uptake by magnetic resonance spin-lock imaging. Magn Reson Imaging
58. Yadav N N, Xu J D, Bar-Shir A, Qin Q, Chan K W Y, Grgac K, Li W B, McMahon M T, van Zijl P C M. Natural D-Glucose as a Biodegradable MRI Relaxation Agent. Magn Reson Med 2014; 72(3):823-828.
59. Gore J C, Brown M S, Mizumoto C T, Armitage I M. Influence of Glycogen on Water Proton Relaxation-Times. Magn Reson Med 1986; 3(3):463-466.
60. Liu Y, Liu F, Iqbal K, Grundke-Iqbal I, Gong C X. Decreased glucose transporters correlate to abnormal hyperphosphorylation of tau in Alzheimer disease. FEBS Lett 2008; 582(2):359-364.
61. Winkler E A, Nishida Y, Sagare A P, Rege S V, Bell R D, Perlmutter D, Sengillo J D, Hillman S, Kong P, Nelson A R, Sullivan J S, Zhao Z, Meiselman H J, Wendy R B, Soto J, Abel E D, Makshanoff J, Zuniga E, De Vivo D C, Zlokovic B V. GLUT1 reductions exacerbate Alzheimer's disease vasculo-neuronal dysfunction and degeneration. Nat Neurosci 2015; 18(4):521-530.
62. Knutsson L, Seidemo A, Rydhog Scherman A, Markenroth Bloch K, Kalyani R R, Andersen M, Sundgren P C, Wirestam R, Helms G, van Zijl P C M, Xu X. Arterial Input Functions and Tissue Response Curves in Dynamic Glucose-Enhanced (DGE) Imaging: Comparison Between glucoCEST and Blood Glucose Sampling in Humans. Tomography 2018; 4(4):164-171.
63. Ma Q, Ineichen B V, Detmar M, Proulx S T. Outflow of cerebrospinal fluid is predominantly through lymphatic vessels and is reduced in aged mice. Nat Commun 2017; 8(1):1434.
64. Ahn J H, Cho H, Kim J H, Kim S H, Ham J S, Park I, Suh S H, Hong S P, Song J H, Hong Y K, Jeong Y, Park S H, Koh G Y. Meningeal lymphatic vessels at the skull base drain cerebrospinal fluid. Nature 2019; 572(7767): 62-66.
65. Chan K W, McMahon M T, Kato Y, Liu G, Bulte J W, Bhujwalla Z M, Artemov D, van Zijl P C. Natural D-glucose as a biodegradable MRI contrast agent for detecting cancer. Magn Reson Med 2012; 68(6):1764-1773.
66. Benner T, Heiland S, Erb G, Forsting M, Sartor K. Accuracy of gamma-variate fits to concentration-time curves from dynamic susceptibility-contrast enhanced MRI: influence of time resolution, maximal signal drop and signal-to-noise. Magn Reson Imaging 1997; 15(3): 307-317.
67. Orton M R, d'Arcy J A, Walker-Samuel S, Hawkes D J, Atkinson D, Collins D J, Leach M O. Computationally efficient vascular input function models for quantitative kinetic modelling using DCE-MRI. Phys Med Biol 2008; 53(5):1225.
68. Iliff J J, Wang M, Liao Y, Plogg B A, Peng W, Gundersen G A, Benveniste H, Vates G E, Deane R, Goldman S A. A paravascular pathway facilitates CSF flow through the brain parenchyma and the clearance of interstitial solutes, including amyloid β. Sci Transl Med 2012; 4(147): 147ra111.
69. Peng W, Achariyar T M, Li B, Liao Y, Mestre H, Hitomi E, Regan S, Kasper T, Peng S, Ding F. Suppression of glymphatic fluid transport in a mouse model of Alzheimer's disease. Neurobiol Dis 2016; 93:215-225.

We claim:

1. A method of assessing the brain lymphatic or glymphatic system and the glucose transporter function on blood-cerebrospinal fluid barrier (BCSFB) of a subject using D-glucose or a D-glucose analog, comprising:
generating a spatial map of water magnetic resonance (MR) signals that are sensitized to changes in D-glucose or a D-glucose analog in cerebrospinal fluid (CSF) of the subject;
observing the spatial map at one or more time points before, one or more time points during, and one or more time points after, raising the blood level of the D-glucose or a D-glucose analog in the subject CSF;
detecting a difference between the MR signals of the spatial map before, during, and after raising the blood level of D-glucose or a D-glucose analog; and
ascertaining a physiological parameter associated with the brain lymphatic or glymphatic system and the glucose transporter function on BCSFB of the subject based on the detected difference.

2. The method of claim 1 in which the D-glucose analog is a sugar that is transported from the blood into the CSF.

3. The method of claim 2 in which the D-glucose analog is at least one of 2-deoxy-D-glucose (2DG), glucosamine, 3-O-methyl-Dglucose (3OMG), Vitamin C, fluorodeoxyglucose (FDG), and mannitol.

4. The method of claim 1, wherein the sensitizing to changes in D-glucose or a D-glucose analog comprises applying one or more radiofrequency (RF) pulses at one or multiple frequencies around a resonance frequency of water.

5. The method of claim 4 wherein the applying one or more RF pulses is such that the MR signal changes after infusion of D-glucose or D-glucose analog are determined predominantly by a change in T2 or T1p relaxation of the water signal due to the chemical exchange of hydroxyl protons in the D-glucose or D-glucose analog with the water protons detected in magnetic resonance imaging (MRI).

6. The method of claim 4 wherein the applying one or more RF pulses is such that MRI signal changes after a D-glucose or a glucose analog infusion are introduced by selective saturation of at least one exchangeable group in the D-glucose or D-glucose analog.

7. The method of claim 4 in which the RF pulses include a sequence of high-power short radiofrequency pulses separated by inter-pulse delay periods of equal or different length with carrier frequencies set at a water resonance frequency.

8. The method of claim 7, wherein the inter pulse delay periods range from 0 to several hundred milliseconds.

9. The method of claim 7, wherein the high-power pulses comprise adiabatic or hard excitation pulses.

10. The method of claim 7, wherein the high-power pulses comprise a train of composite pulses with shifted phases causing an excitation profile that magnetically labels exchanging protons in D-glucose or D-glucose analogs.

11. The method of claim 7, wherein the high-power pulses comprise spin-lock pulses.

12. The method of claim 4, wherein the RF pulses are applied according to one of an on-resonance variable delay multiple pulse (onVDMP) scheme, a spin-lock scheme, and a Carr-Purcell-Meiboom-Gill (CPMG) scheme.

13. The method of claim 1, further comprising determining the rate of change and amplitude of the MR signals due to the presence of D-glucose or D-glucose analog.

14. The method of claim 13, further comprising determining the glucose transporter function on the BCSFB based on the rate of change and amplitude of the MR signal.

15. The method of claim 1, further comprising determining the clearance or decay rate and amplitude of the MR signal due to the change of the D-glucose or D-glucose analog.

16. The method of claim 15, further comprising assessing the brain lymphatic or glymphatic system based on the clearance or decay rate and amplitude of the MR signal change.

* * * * *